United States Patent [19]

Angel et al.

[11] 3,973,189
[45] Aug. 3, 1976

[54] HEMATOLOGY SYSTEM

[75] Inventors: Henry R. Angel, Trumbull; Arthur R. Oefinger, Stratford; James W. Hennessy, Trumbull, all of Conn.

[73] Assignee: General Science Corporation, Bridgeport, Conn.

[22] Filed: Jan. 27, 1975

[21] Appl. No.: 544,643

Related U.S. Application Data

[63] Continuation of Ser. No. 253,281, May 15, 1972, abandoned.

[52] U.S. Cl. ........................................... 324/71 CP
[51] Int. Cl.² ............................................ G01N 27/00
[58] Field of Search .............................. 324/71 CP

[56] References Cited
UNITED STATES PATENTS

| | | | |
|---|---|---|---|
| 3,439,267 | 4/1969 | Coulter et al. | 324/71 CP |
| 3,757,213 | 9/1973 | Coulter et al. | 324/71 CP |

OTHER PUBLICATIONS

Taylor, W. B., "A Versatile Cell Detector for Cell Volume Measurements" Med. & Biol. Engng., vol. 8, No. 3, pp. 281–290, 1970.

Primary Examiner—John K. Corbin
Assistant Examiner—Rolf Hille
Attorney, Agent, or Firm—Weingarten, Maxham & Schurgin

[57] ABSTRACT

A system for counting electrical pulses representing red and white blood cells and for determining hematocrit, mean corpuscular volume and hemoglobin in association with the blood cell counts. The system includes a blood cell transducer through which a blood sample is caused to flow and operative to produce electrical pulses in response to the passage of cells through a metering aperture. Red and white blood cell counts are electronically accumulated during respective analytical runs and logic circuitry is provided for determining, during a red blood cell counting run, mean corpuscular volume and hematocrit. The system can also include correction circuitry to correct for the coincident passage of cells through the metering aperture.

2 Claims, 14 Drawing Figures

FIG. 2A
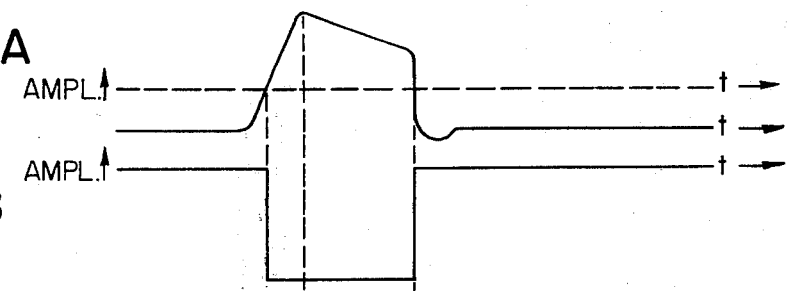
FIG. 2B
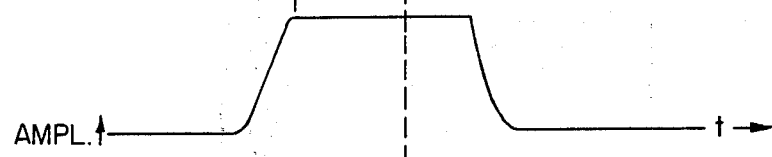
FIG. 2C
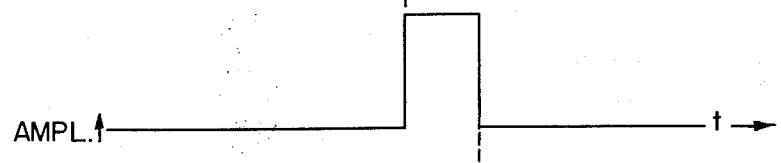
FIG. 2D
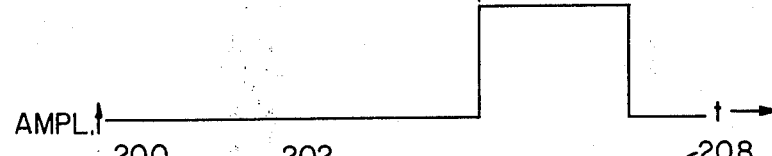
FIG. 2E
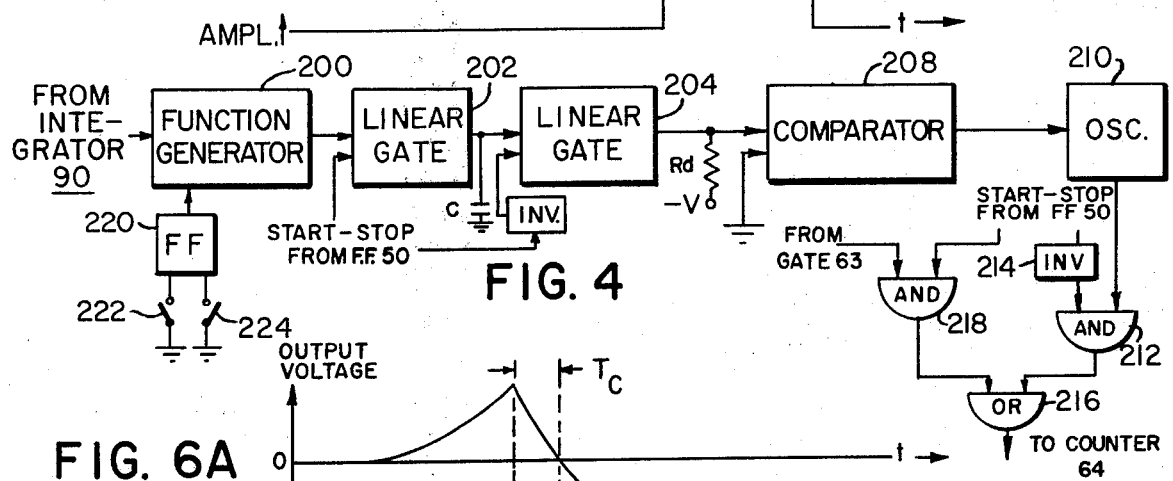
FIG. 4
FIG. 6A
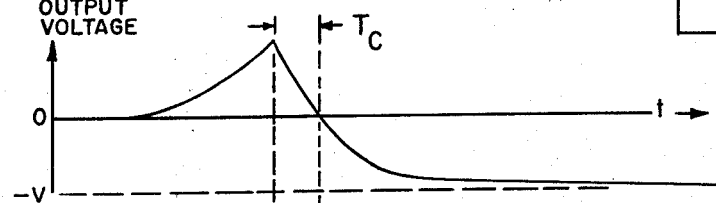
FIG. 6B
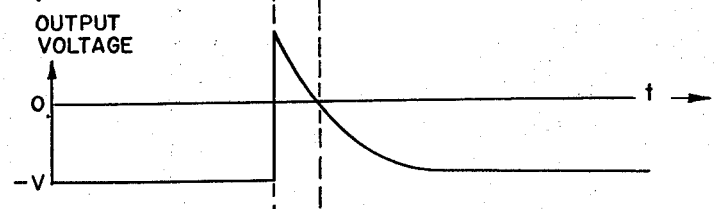
FIG. 6C

HEMATOLOGY SYSTEM

This is a continuation of application Ser. No. 253,281, filed May 15, 1972, now abandoned.

FIELD OF THE INVENTION

This invention relates to particle counters and more particularly to a particle counting system for the counting of red and white blood cells and for determining certain hematological parameters in association with the cell counts.

BACKGROUND OF THE INVENTION

In systems for counting blood cells or other particles suspended in a liquid sample, a pair of electrodes are provided within a fluid path having an aperture disposed therebetween through which the particle-containing liquid flows. The impedance of the fluid path as sensed by the electrodes is materially altered by the presence of a particle within the aperture giving rise to electrical pulses which are electrically counted and which correspond to the number of particles passing through the aperture. Means are usually employed for metering a known volume of particle-containing liquid such that a particle count is provided for a predetermined liquid volume. In the hematological analysis of blood a variety of parameters in addition to cell counts are useful and have been provided either by respective analytical instruments or by relatively complex multiple parameter systems.

SUMMARY OF THE INVENTION

In accordance with the present invention, a system is provided which is embodied in a single analytical instrument for counting red and white blood cells and for determining from these counts mean corpuscular volume (MCV) and hematocrit (HCT). Hemoglobin (HGB) measurement is also accomplished in association with the white blood cell count. The invention requires only two dilutions of sample blood to provide all output determinations.

Briefly, the invention comprises a blood cell transducer through which a properly diluted blood sample is caused to flow and operative to produce electrical pulses in response to the passage of cells through a metering aperture therein. The blood sample is also caused to flow through a hemoglobin transducer which is operative to provide by electro-optical colorometric means an output signal representative of the hemoglobin content of the analyzed sample. Electronic counting circuitry is provided to accumulate red and white blood cell counts during respective analytical runs and to provide output indications of cell count. The system also features associated logic circuitry for determining during a red blood cell counting run, hematocrit and mean corpuscular volume. Correction for the coincident passage of cells through the metering aperture can also be provided.

DESCRIPTION OF THE DRAWINGS

The invention will be more fully understood from the following detailed description taken in conjunction with the accompanying drawings, in which:

FIGS. 2A–2E are signal diagrams useful in illustrating operation of the system of FIG. 1;

FIG. 4 is a diagrammatic representation of automatic coincidence correction circuitry embodied in the invention;

FIGS. 6A–6C are signal diagrams useful in illustrating operation of the circuitry of FIG. 4.

DETAILED DESCRIPTION OF THE INVENTION

Figure 1:
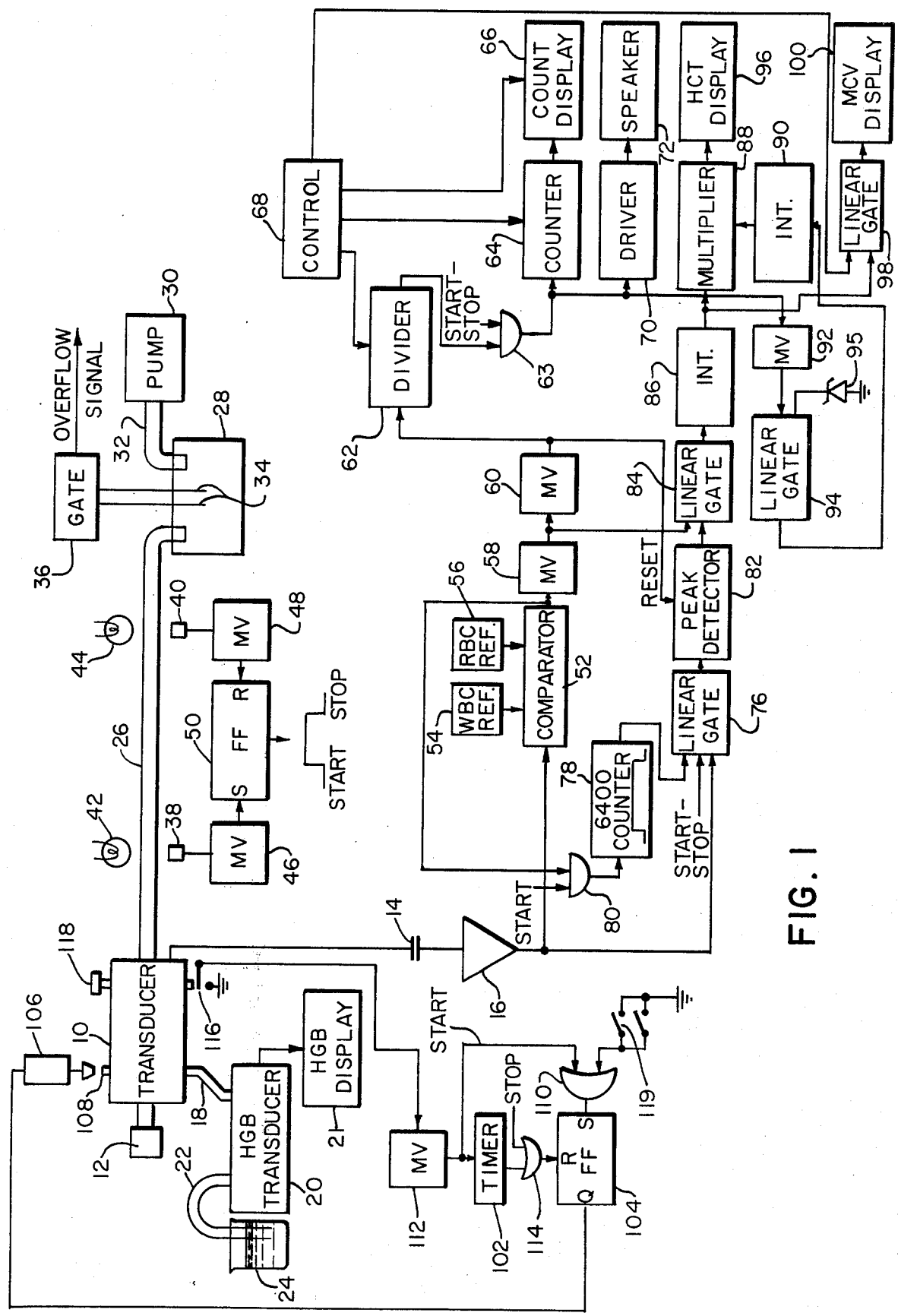
FIG. 1 is a diagrammatic representation of a system according to the invention.

The system embodying the invention is operative to determine from only two dilutions of blood sample hematology parameters most commonly required in practice; namely, red blood cell count (RBC), white blood cell count (WBC), hemoglobin (HGB), hematocrit (HCT), and mean corpuscular volume (MCV). Using a first sample dilution, RBC, HCT, and MCV are determined, while WBC and HGB are determined from a second sample dilution. The system is shown in FIG. 1 and includes a blood cell transducer 10 having a pair of electrodes therein disposed on respective opposite sides of an aperture which is contained within a removeable support member 12 to permit alignment of the aperture within cell 10 and to permit its easy removal for cleaning and replacement. The passage of blood cells through the aperture causes an impedance change which results in the production of electrical pulses which are AC coupled via capacitor 14 to the input of a high input impedance, low noise, high gain operational amplifier 16. The output pulses from amplifier 16 are processed in a manner to be explained to provide the intended output indications.

The transducer 10 includes a fluid input tube 18 coupled to the fluid output of a hemoglobin transducer 20 which, in turn, has a fluid input tube 22 coupled to a sample flask 24 containing a properly diluted blood sample for analysis. The hemoglobin transducer 20 drives a suitable display 21. The fluid output of transducer 10 is coupled to flow tube 26 which terminates in a waste bottle 28 to which a vacuum pump 30 is coupled by way of a connecting tube 32. The waste bottle is sealed such that operation of pump 30 causes sample liquid to be drawn from flask 24 through transducer 20, transducer 10, and thence through tube 26 into the waste bottle. Waste bottle 28 also includes a pair of electrodes 34 disposed therein at a predetermined height to sense liquid at an overflow level, these electrodes being connected to a gate circuit 36 which provides an overflow signal in response to the presence of liquid at the level of the electrodes 34.

The tube 26 has a predetermined bore dimension to contain a known volume of liquid therein between first and second reference positions, and means are provided at these reference positions to respectively detect the passage of liquid within tube 26 to define a known liquid volume within which cell counts are accumulated. In the illustrated embodiment, a first photosensor 38 is disposed at the reference position nearest transducer 10 while a second photosensor 40 is disposed at a reference position downstream from sensor 38. Respective lamps or other illumination sources 42 and 44 are provided for illumination of respective photosensors 38 and 40 through tube 26 which in this embodiment is of light transmissive material such as glass. The photosensors 38 and 40 are each operative to provide an output signal upon the passage of liquid past the respective sensing position, and these signals are employed to define a time representing a selected liquid volume within which particle counts are taken.

The output signals from photosensors 38 and 40 are applied to respective multivibrators 46 and 48, the output signals of which are applied, respectively, to the set and reset terminals of a flip-flop 50. The output signal from flip-flop 50 is a gate signal as illustrated having a first signal transition labeled "start" and a second opposite signal transition labeled "stop" and employed to define a time interval within which a cell count is performed. One photoelectric volume metering technique for cell counting is described in U.S. Pat. No. 3,577,162. It will be appreciated that other techniques, photoelectric and otherwise, can be employed for sensing the passage of liquid through tube 26 to define a sample volume in which a count is performed. As an alternative, a defined time interval can be employed within which a particle count is taken and representative of a known liquid volume rather than monitoring liquid flow as such.

The electrical ouput of amplifier 16 is applied to a comparator 52 which receives as a reference signal either a first threshold level from white blood cell reference 54 or a second threshold level from red blood cell reference 56, depending on the particular type of cells being analyzed. The comparator 52 provides output pulses in response to received pulses which are above the predetermined threshold and which are applied to a first multivibrator 58 and thence to a second multivibrator 60, the output of which is applied to a divider 62. The output of divider 62 is applied via an AND gate 63 to a counter 64 which, in turn, drives a count disply 66, typically a multi-digit numerical display. The start-stop gate signal from flip-flop 50 is applied as an enable signal to AND gate 63. A control circuit 68 is coupled to divider 62, counter 64 and display 66 to adjust operation of the counting circuitry in accordance with red or white cells being analyzed. The output of divider 62 is also coupled to a driver 70 which energizes a loudspeaker 72 or other audible indicator to provide an audible indication of count cadence useful in permitting operator determination of erroneous system operation.

The output of amplifier 16 is also applied to one input of a linear analog gate 76, a second input to gate 76 being provided by the start-stop signal from flip-flop 50. A third input to gate 76 is provided by a counter 78 which provides a predetermined number of pulses when energized by a signal from AND gate 80. The AND gate 80 is energized by the output signal from comparator 52 and the start-stop signal. The output of gate 76 is applied to a peak detector 82 which is reset by a signal from multivibrator 60. The output of the peak detector is applied via a linear gate 84 to an integrator 86. Gate 84 also receives an enabling signal from the output of multivibrator 58.

The output of integrator 86 is applied to one input of a multiplier 88 which also receives a second input from an integrator 90. A signal from gate 63 is applied to a multivibrator 92 and thence via a linear gate 94 to integrator 90. A reference signal is also applied to gate 94 by Zener diode 95. The output signal from multiplier 88 is employed to energize a hematocrit display 96 such as a suitably calibrated meter. The output of integrator 86 is also applied via a linear gate 98 to drive an MCV display 100 which can also be a meter display. Gate 98 receives an enabling signal from control circuit 68 during red cell counting since MCV is determined from the red cell count.

The vent port 108 of transducer 10 is selectively opened and closed by means of solenoid 106 which is energized by a signal from flip-flop 104. The flip-flop 104 receives a set signal from an OR gate 110 and a reset signal from an OR gate 114. The OR gate 110 receives as one input a signal from a count start switch 119 which is a panel control for initiating red or white cell counting, and also receives an input signal from a multivibrator 112. The multivibrator 112 also drives a timer 102 which provides an input signal to OR gate 114. The start stop signal from flip-flop 50 is also applied as an input to OR gate 114. The multivibrator 112 is energized in response to actuation of switch 116 by the priming button 118.

Upon actuation of the count start switch 119, flip-flop 104 is set causing an output signal to be applied to solenoid 106 to cause closure of the transducer vent port 108. Sample liquid is drawn by operation of pump 30 from flask 24 through transducer 20, transducer 10 and thence through flow tube 26 into the waste bottle 28. Pulses generated by the passage of particles through the transducer aperture are applied via capacitor 14 to amplifier 16 and these pulses are counted for an interval defined by the start-stop gate provided by flip-flop 50 such that a cell count is taken for a known volume of liquid.

After amplication, the pulses from transducer 10 are applied to comparator 52 which provides output pulses in response to received pulses which exceed the predetermined threshold voltage as provided by white threshold reference 54 or red threshold reference 56, depending upon whether red blood cells or white blood cells are being counted. The comparator output pulses are delayed by respective multivibrators 58 and 60 and applied to a divider 62 which generates an output pulse for every predetermined number of input pulses. In the illustrated embodiment, the divider 62 has a division ratio of 64 in the case of red blood cell counting and a division ratio of 128 in the case of white blood cell counting. Thus, the divider provides an output pulse for every 64 input pulses received during red blood cell counting, and one output pulse for every 128 input pulses received during white blood cell counting. The specific division ratios are a matter of choice in accordance with the sample dilutions employed and the nature of the particular circuitry being utilized in a specific implementation. Divider operation is controlled by a signal provided by control circuitry 68 to provide the intended division ratio in accordance with the type of cells being analyzed.

The output pulses from divider 62 are applied via an AND gate 63 to a counter 64 which increments to a number representing the total number of pulses received during the predetermined sampling time, this count being displayed on a multidigit indicator or other count display 66. The AND gate 63 is enabled by the start-stop signal from flip-flop 50 which provides a measure of the sampling time within which a count is taken. As noted above, the output pulses from divider 62 are also applied to a driver 70 operative to energize a loudspeaker 72 to provide an audible indication of count cadance.

After an analytical run, the transducer 10 is purged of remaining amounts of an analyzed sample liquid and gas bubbles which may be present and is also primed for a subsequent analytical run by means of priming button 118, the operation of which will be described hereinbelow. Depression of priming button 118 causes actuation of switch 116 which, in turn, energizes multivibrator 112. The output signal from multivibrator 112 is transmitted via OR gate 110 to flip-flop 104 to cause the output signal thereof to actuate vent solenoid 106 to cause closure of the vent port 108. The multivibrator 112 also provides a signal to timer 102 operative after a specified interval of time to provide an output signal via OR gate 114 to reset flip-flop 104 to cause deactivation of the vent solenoid 106. The OR gate 114 is also operative in response to the trailing edge of the start-stop gate signal to cause application of a reset signal to flip-flop 104. Thus, actuation of the transducer priming control 118 causes closure of the transducer vent for a predetermined interval of time to permit purging of sample liquid and gas bubbles from the transducer and priming for a subsequent analytical run.

Hematocrit is performed by determining the red blood cell count and the mean corpuscular volume of the analyzed sample and multiplying these determinations to compute hematocrit. During red blood cell counting, the output of AND gate 63 is applied to a multivibrator 92 which provides pulses of uniform width to one input of an linear gate 94. The other input of linear gate 94 is coupled to a Zener reference diode 95 which provides a reference potential for the linear gate 94. Gate 94 is operative to provide output pulses of standardized width as determined by the multivibrator 92 and standardized height as determined by Zener diode 95, these output pulses being applied to integrator 90. The integrator 90 provides an output voltage proportional to red blood cell count and this integrated output voltage is applied as one input to multiplier 88 for use in the hematocrit computation.

The mean cell volume determination which is employed in the hematocrit determination and also for separate output indication is measured by averaging the volume of a predetermined number of cells. The output pulses from amplifier 16, shown in FIG. 2A, are applied to an input of a linear gate 76. The output pulses of comparator 52, depicted in FIG. 2B, are applied via AND gate 80 to counter 78 which provides a predetermined number of enabling pulses to linear gate 76 during the sampling interval defined by the start-stop signal provided by flip-flop 50. In the embodiment described 6400 pulses are provided by counter 78 in response to the corresponding number of cells detected by transducer 10. The linear gate 76 provides 6400 output pulses within the sampling interval, each of a height representative of the height of the corresponding pulse received from amplifier 16. These output pulses the height of which is proportonal to cell volume are then applied to peak detector 82. The peak detected output signal, shown in FIG. 2C, is applied to linear gate 84 which is enabled by a gate signal from multivibrator 58, shown in FIG. 2D, and which produces an output signal of standardized width and of an amplitude representative of the peak amplitude of the corresponding received signals. This signal from gate 84 is applied to integrator 86. After a time determined by multivibrator 60, a reset pulse (FIG. 2E) is applied to peak detector 82 to reset the circuit for receipt and processing of the next pulse.

The height of the pulses provided by transducer 10 and by associated amplifier 16 is proportional to the volume of corresponding blood cells passing through the metering aperture of transducer 10, and the integrator 86 provides an output signal representing mean cell volume. Since a constant number of pulses is employed for MCV determination, the output signal of integrator 86 is calibrated to represent the mean cell volume without necessity for division of the totalized cell volume by the number of pulses. This integrated output signal is applied as one input to multiplier 88 which provides an output signal representing hematocrit measurement for presentation on a suitable display 96. The gain of the circuitry for providing the RBC and MCV signals to multiplier 88 and the multiplier gain are adjusted to provide an intended hematocrit output reading for predetermined input signal conditions.

The output of integrator 86 is also employed to energize via a linear gate 98 an MCV display 100 for indication of mean corpuscular volume. Gate 98 is enabled by a signal from control 68 which provides a gating signal only when red blood cell counting is accomplished since MCV is derived from the red blood cell count.

Figure 3:
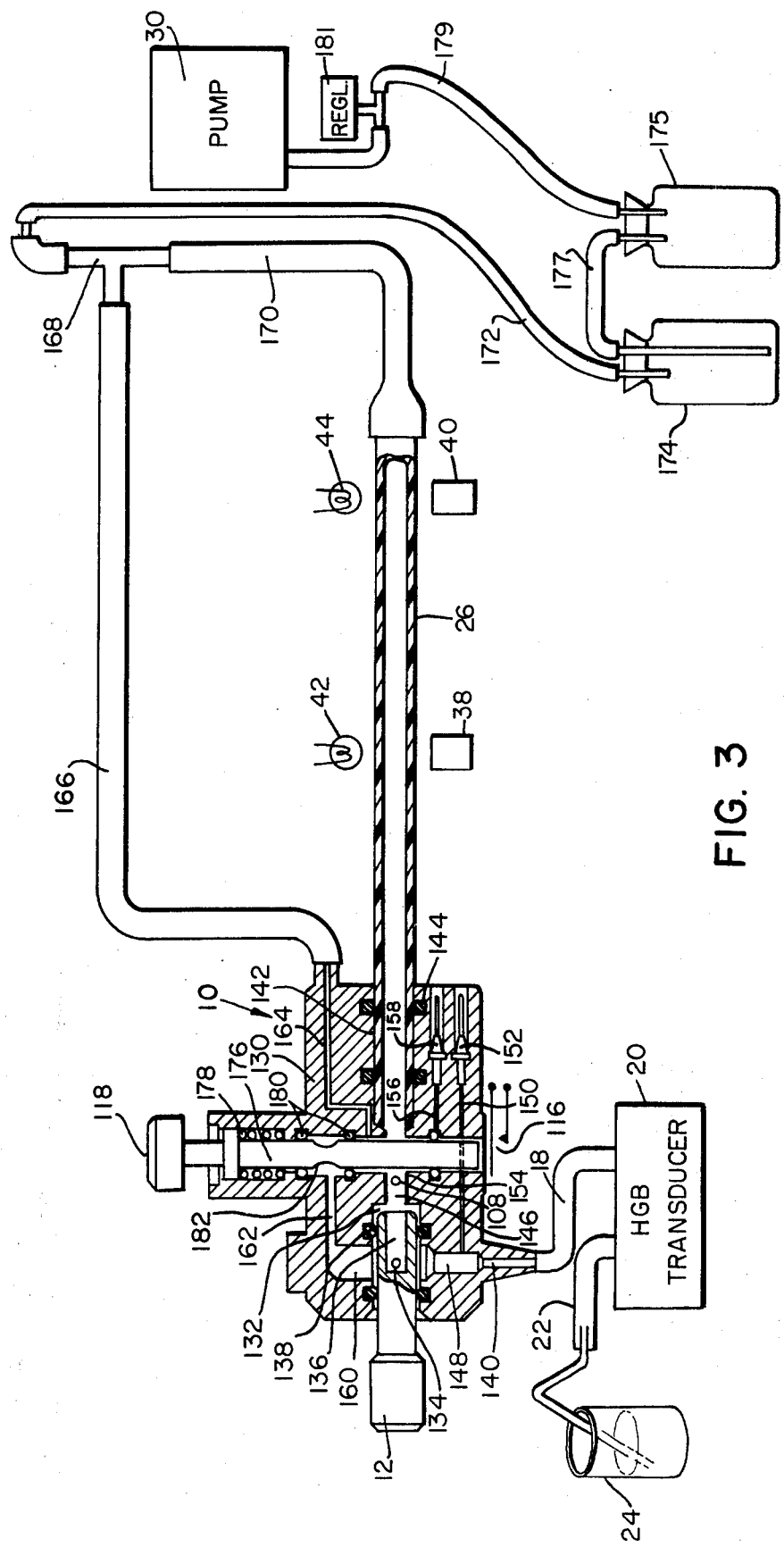
FIG. 3 is a diagrammatic representation of the blood cell transducer and associated hydraulic apparatus embodied in the system of FIG. 1.

The transducer 10 and associated hydraulic system is shown in greater detail in FIG. 3 and includes a body 130 typically formed of a clear plastic material such as Plexiglass which is easily cleaned and compatible with the liquid being analyzed. The transducer is itself the subject of copending application Ser. No. 247,991, filed Apr. 27, 1972, now U.S. Pat. No. 3,781,675 entitled Self Priming Conductivity Cell. An opening 132 is provided in one end of body 130 to accommodate a support member 12 having an aperture 134 through which a blood sample is caused to flow for analysis. Support member 12 includes an opening 136 formed in an end thereof and communicating with one side of aperture 134 disposed within a wall of member 12. The aperture is typically formed wihin a ruby plate and is sized to permit passage of the blood cells to be counted. Sealing elements such as O-ring 138 are provided within grooves formed around opening 132 to maintain support member 12 in sealed engagement therein. An input passage 140 communicates between aperture 134 and an input port to which tube 18 is connected.

An opening 142 at the opposite end of body 130 receives tube 26 which is maintained in sealed engagement therein by means of O-rings 144. A passage 146 communicates between openings 142 and 132 to provide a fluid path therebetween. A first electrode 148 of generally semi-cylindrical form is provided within an enlarged portion of passage 140 and is connected via a wire 150 to a terminal 152 disposed within the lower portion of body 130. A second electrode 154 of cylindrical configuration is provided within passage 146 and connected via a wire 156 to a second terminal 158 also disposed within the lower portion of the cell body adjacent electrode 152. Electrical connection is made to the transducer terminals by a suitable connector for coupling the transducer output to amplifier 16 (FIG. 1).

The fluid path for analysis is from sample flask 24 through hemoglobin transducer 20 and thence through passage 140, aperture 134, passage 146 and into tube 26. A chamber 160 is provided above support member 12 and in fluid communication with input passage 140. The chamber 160 communicates via a passage 162 with a slide valve assembly and thence via a passage 164 through a fluid output port coupled to a tube 166 which is connected via a T-connection 168 to a tube 170 connected to flow tube 26 and also via tube 172 to a waste bottle 174. The waste bottle 174 is coupled to a second bottle 175 via a tube 177, and bottle 175, in turn, is connected by a tube 179 to vacuum pump 30. A pressure regulator 181 can be provided as shown to maintain an intended pressure level. Pump 30 is operative to draw a negative pressure and cause sample liquid to flow for analysis. Bottle 174 serves as an accumulator to maintain substantially uniform flow since waste liquid is conveyed into bottle 175 for collection.

Referring again to transducer 10, the valve assembly includes a manually operable button 118 connected to a stem 176 slideably disposed within an associated passage in body 130. A spring 178 urges stem 176 into a raised position in the absence of force applied to button 118. A pair of O-ring 180 are provided around the stem chamber to sealingly engage stem 176 within the chamber. A plurality of elongated channels 182 are provided in stem 176 extending axially thereof and being disposed between O-ring 180 with the stem in its raised position. In this raised position, fluid within passage 162 cannot be drawn into passage 164 since a fluid seal is provided by stem 176 cooperating with O-rings 180. When, however, the button 118 is depressed causing the channels 182 to straddle the lower O-ring 180 and to extend slightly above and below the upper and lower surfaces of this O-ring, fluid can flow between passages 162 and 164 and thence via tubing 166 and 172 to the waste bottles.

During operation, the button 118 is in its raised position and upon closure of vent 108, sample liquid is caused to flow by action of pump 30 through transducer 10 and tube 26 for analysis. Bubbles which tend to form such as by electrolysis during an analytical run or which are present in a liquid sample rise to the top of chamber 160 away from the path of liquid flow and do not interfere with the accuracy of the cell counting operation as no bubbles are drawn through the aperture 134. After an analytical run, the button 118 is depressed either manually or by suitable automatic control such as an electrically operated solenoid to cause liquid and bubbles in chamber 160 to be drawn via passages 162 and 164 into output tubing 166 for conveyance to the waste bottles. The hydraulic impedance of this purging path is lower than that of the cell counting path, and thus, during purging operation, liquid flow tends to by-pass the aperture and to flow into chamber 160 for removal from the transducer.

After purging of the transducer, vent 108 is opened and with button 118 depressed, air is drawn into the vent and through aperture 134 in a direction opposite to that of liquid flow during a counting run and thence via passages 162 and 164 and tubing 166 to the waste bottles. Air and bubbles within flow tube 26 are drawn into the waste bottles during this operating state. The reverse flow of air through the aperture causes backflushing of debris which can accumulate in the aperture and the transducer therefore provides not only purging of the cell for a subsequent analytical run but also automatic cleaning of the aperture between runs.

During cell counting, more than one blood cell can pass through the transducer aperture at the same time, causing the erroneous detection of these plural cells as a single cell. The measured cell count is therefore somewhat lower than the actual count. The number of cells being counted by the novel system is sufficiently large to predict statistically the amount of coincidence error and to correct the error by use of a computed correction chart. As a further feature of the invention, automatic coincidence correction can be provided by the circuitry shown in FIG. 4 and described in conjunction with the function plot of FIG. 5 and signal diagrams of FIG. 6.

Figure 5:
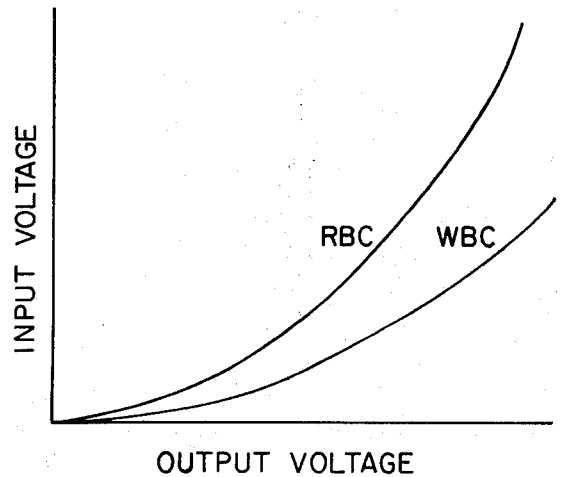
FIG. 5 is a plot of coincidence correction functions useful in illustrating operation of the circuitry of FIG. 4.

Referring now to FIG. 4, the output signal of integrator 90 is applied to a function generator 200 which provides an output versus input voltage function of generally exponential form for both RBC and WBC, as depicted in FIG. 5. The output voltage $v_c$ of function generator 200 is the corrected voltage representing the corrected red blood cell count and which is higher than the measured voltage received as an input. This output voltage is applied to an input of a linear gate 202, the enable input of which is provided by the start-stop signal from flip-flop 50 (FIG. 1). The output signal from linear gate 202, depicted in FIG. 6A, is applied to a capacitor C, coupled to ground, and is applied to one input of a linear gate 204 which receives an inverted version of the start-stop gate signal provided via an inverter 206. The output of gate 204 is coupled via a resistor $R_d$ to a source of negative potential $-v$, and is also coupled to an input of a zero-sensing comparator 208 which has an input coupled to a source of reference potential such as ground. The signal appearing at the output of gate 204 is as shown in FIG. 6B. The output of comparator 208 is coupled to an oscillator 210 the output of which, in turn, is coupled to one input of an AND gate 212. The AND gate 212 also receives the start-stop gate signal applied via an inverter 214. The output of AND gate 212 is coupled to one input of an OR gate 216 the output of which is a series of pulses (FIG. 6C) applied to the counter 64 (FIG. 1). The second input of OR gate 216 is provided by an AND gate 218 which receives as input signals the start-stop gate signal and the output signals from gate 63 coupled to divider 62. The correction function is different for red blood cell counts and white blood cell counts and is determined by a control signal provided by a flip-flop 220 which is set or reset by respective switches 222 and 224.

During operation, gate 202 is activated during the interval of the start-stop signal, while gate 204 is deactivated during this interval by application of the inverted gating signal thereto. As shown in the signal diagrams of FIG. 6, the correction voltage is transferred by linear gates 202 and 204 to the input of comparator 298 which is enabled for the time $T_c$ that the applied signal is of positive sense. Comparator 208 provides a signal to oscillator 210 for the time interval $T_c$, causing the generation of pulses during this interval of a number to be added to the measured count to correct for coincidence error.

The AND gate 218 is gated on during the start-stop signal, while AND gate 212 is gated on after this signal. The measured pulses from divider 62 and gate 63 (FIG. 1) are thus provided by way of OR gate 216 to counter 64 and the correction pulses are then applied to counter 64 by gate 212 to drive the counter to a corrected value.

Figure 7:
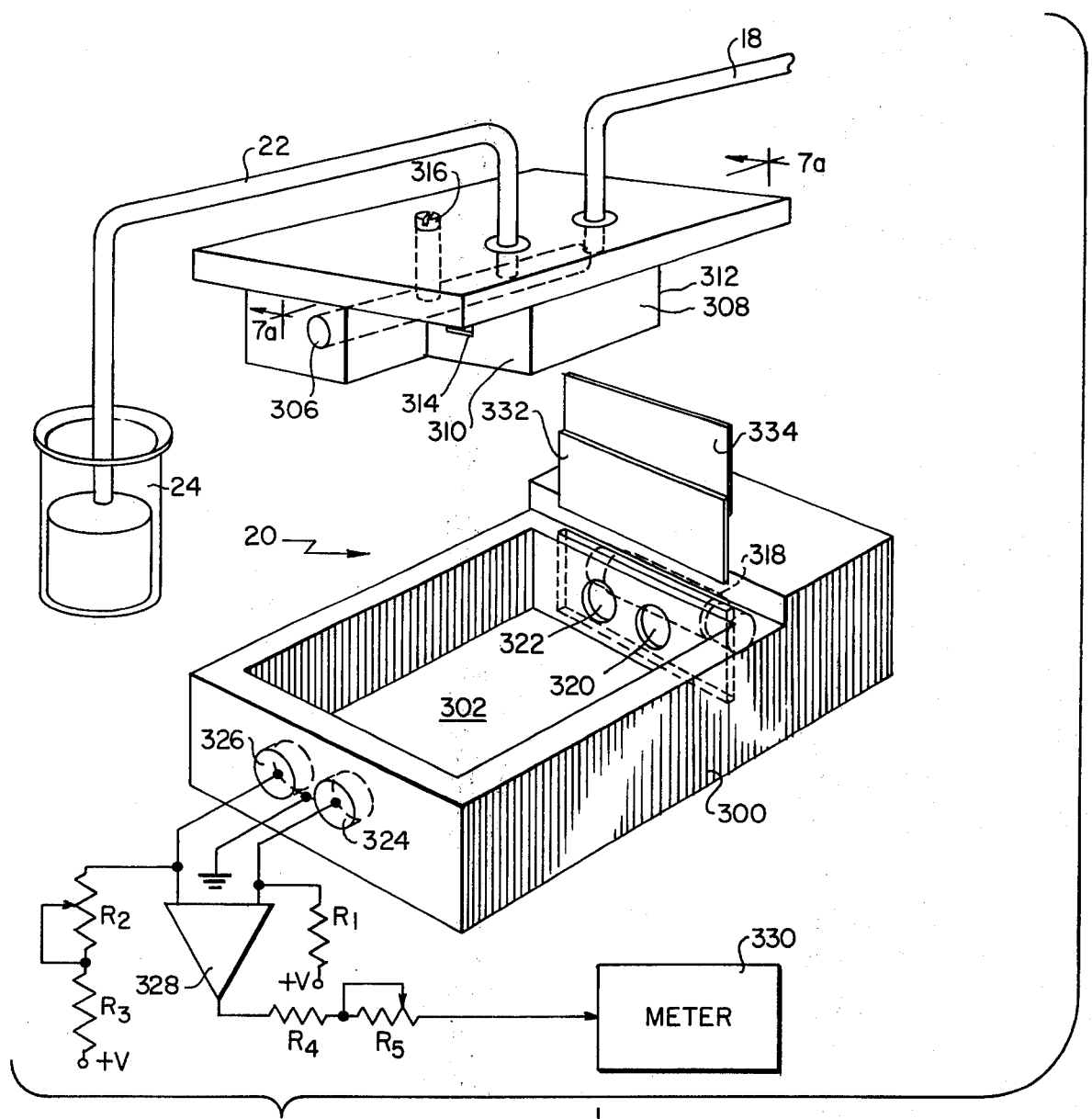
FIG. 7 and 7a are a partial pictorial and partial schematic representation of a hemoglobin transducer embodied in the invention.
Figure 7A:
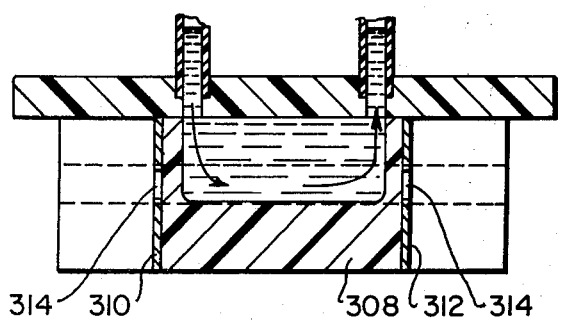

The hemoglobin transducer 20 is shown in FIG. 7 and is operative to compare the quantity of light passing through a sample of diluted blood with a reference light to compute hemoglobin content of the analyzed sample. The transducer includes a generally rectangular housing 300 having an opening 302 therein for receiving a cover assembly 304 which contains a light transmitting passage 306 extending therethrough and an enclosure 308 through which sample liquid is caused to flow for analysis. The enclosure 308 is formed of a light transmissive material, typically a plastic, and is secured in sealing relationship to the bottom surface of the cover plate of the cover assembly 304. An input port and an output port are provided through the cover plate communicating with and output ends of enclosure 308, these ports being coupled to respective tubes 22 and 18. The input tube 22 receives sample liquid from a sample flask 24, while the output tube 18 conveys liquid through the transducer 10 for cell counting as described above.

First and second opaque masks 310 and 312 are respectively provided on the front and back ends of enclosure 308, each having an aperture 314 provided therein at a position near the lower portion of the enclosure, as illustrated. A machine screw 316 is provided in threaded engagement with an opening in the cover assembly 304 for adjustable disposition within opening 306 to control the light transmission therethrough. The cover assembly is installed on housing 300 with the enclosure 308 and opening 306 within the opening 302. An elognated light source such as a lamp 318 is provided within one end of housing 300 in alignment with first and second apertures 320 and 322, which, in turn, are in alignment with the aperture 314 of mask 312 and the confronting end of opening 306, respectively.

A pair of photosensors 324 and 326 are provided in the opposite end of housing 300 in light receiving relationship with the aperture 314 of mask 310 and the confronting end of opening 306. The light source is energized by a suitable energy source (not shown). One terminal of the photosensors 324 and 326 is connected in common to a source of ground potential and the other terminal of the respective photosensors is connected to respective inputs of a differential input amplifier 328. A source of positive potential +V is applied via a resistor R1 to one input of amplifier 328, while the positive potential is applied to the other input thereof via series connected resistors R2 and R3. Resistor R2 is adjustable to control the precise voltage applied to the reference input of amplifier 328. The output of the amplifier is coupled via resistor string R4 and R5 to an indicator such as a meter 330. Resistor R5 is also an adjustable resistor to control the output voltage applied to meter 330.

A light difusing plate 332 is provided between light source 318 and apertures 320 and 322 to provide even distribution of light, and a 5400 Angstrom filter 334 is provided in light transmitting relationship with the diffusing plate 332 to provide filtered light of appropriate wavelength for reaction with the blood sample being analyzed in order to detect hemoglobin content, as is well known in the art.

The hemoglobin determination is provided on the same diluted sample as the white blood cell count and the lysing agent employed in a white blood cell count lyses the red blood cells and releases hemoglobin which is detected by the transducer 20. The released hemoglobin is reacted with potassium cyanide-potassium ferricyanide reagent to form a cyan-methemoglobin complex.

In operation, sample fluid is caused to flow through the enclosure 308 and light from aperture 320 is caused to be transmitted through the length of enclosure 308 for reception by photosensor 304. Light from aperture 322 is transmitted through opening 306 for reception by photosensor 326. The amount of reference light transmitted through opening 306 is adjustable by means of screw 316. It is noted that the light transmitted through the sample liquid within enclosure 308 is at a position near the bottom of the enclosure allowing a space above the light transmission path where bubbles, which can be present in a sample, can rise to a position which does not interfere with light transmission. The output signal provided by photosensor 324 is of a magnitude representative of the transmissivity of the optical path through the analyzed sample, while the light transmitted through opening 306 is a measure of the reference level of light provided by the light source 318. Amplifier 328 thus receives a reference signal from sensor 326 and a signal from sensor 324 which varies in accordance with the hemoglobin content of the analyzed sample. The differential input amplifier provides an output signal representative of the difference between the reference sensor and the hemoglobin sensor, this difference being directly representative of hemoglobin content. The system operating levels are initially adjusted by means of resistors R2 and R5 to provide calibrated output levels for proper energization of meter 330.

Various modifications and alternative implementations will now occur to those versed in the art without departing from the spirit and true scope of the invention. Accordingly it is not intended to limit the invention by what has been particularly shown and described except as indicated in the appended claims.

What is claimed is:

1. A blood cell analysis system comprising:
means for providing electrical pulses in response to blood cells suspended in a liquid sample passing through an aperture through which said sample liquid is caused to flow;
means including a selected threshold level and operative in response to said electrical pulses having an amplitude above said threshold level to provide cell output pulses;
means for providing a start signal representative of the commencement of an analytical run;
a counter enabled by said start signal and operative in response to said cell output pulses to provide a predetermined fixed number of counter output pulses;
a first linear gate enabled by said start signal and operative to provide a predetermined number of gate output pulses each of a height proportional to the volume of a corresponding blood cell in response to said electrical pulses and said predetermined fixed number of received counter output pulses;
a peak detector operative in response to said gate output pulses to provide detector output pulses each having a uniform amplitude representative of the peak amplitude of corresponding ones of said gate output pulses and representative of the volume of a corresponding blood cell;
a first multivibrator receiving said cell output pulses and providing uniform width gating pulses;
a second linear gate receiving and detector output pulses and said uniform width gating pulses and providing a predetermined number of output pulses each of the same width and of a uniform amplitude representative of the amplitude of corresponding ones of said detector output pulses;

a first integrator operative in response to the output pulses from said second linear gate to provide a calibrated analog output signal representative of mean corpuscular volume;

divider means operative in response to said cell output pulses to provide a plurality of pulses of a number representative of the number of cells in a predetermined volume of sample liquid;

a second integrator operative in response to said plurality of pulses to provide a second analog signal of a magnitude representative of blood cell count for a predetermined volume of sample liquid;

a function generator operative in response to said second analog signal to provide a corrected analog output signal of a magnitude representative of blood cell count corrected for coincidence error;

a third linear gate operative in response to said corrected output signal and for the interval of said start signal to charge a capacitor to a voltage representative of blood cell count;

a fourth linear gate operative upon discontinuance of said start signal to provide an output signal derived from the discharge of said capacitor and defining a time interval representative of coincidence error correction;

a comparator coupled to the output of said fourth linear gate and operative to provide a gate signal of duration equal to said time interval and representative of coincidence error correction;

an oscillator for providing a plurality of correction pulses during the duration of said gate signal;

a first AND gate enabled for the duration of said start signal to pass said plurality of pulses from said divider means;

a second AND gate enabled upon termination of said start signal to pass said correction pulses; and an OR gate for receiving said output pulses from said first AND gate and said correction pulses from said second AND gate for providing the sum of said received pulses thereby to provide a corrected plurality of pulses of a number corrected for coincidence error.

2. The system according to claim 1 further comprising:

a multiplier operative in response to said analog output signal from said first integrator and to a signal derived from said corrected plurality of pulses from said OR gate to provide an output signal representative of hematocrit.

* * * * *

UNITED STATES PATENT AND TRADEMARK OFFICE
CERTIFICATE OF CORRECTION

PATENT NO. : 3,973,189
DATED : August 3, 1976
INVENTOR(S) : Henry R. Angel, Arthur F. Oefinger and James W. Hennessy It is certified that error appears in the above-identified patent and that said Letters Patent are hereby corrected as shown below:

Column 4, line 33, "amplication" should read "amplification".
Column 6, line 41, "O-ring" should read "O-rings". Column 7, lines 18 and 22,"O-ring" should read "O-rings". Column 8, line 49, "comparator 298" should read "comparator 208".
Column 9, line 9, "with and output ends" should read "with the input and output ends"; line 25, "elognated" should read "elongated". Column 10, line 63, "receiving and detector" should read "receiving said detector".

Signed and Sealed this

Fourth Day of October 1977

[SEAL]

Attest:

RUTH C. MASON
*Attesting Officer*

LUTRELLE F. PARKER
*Acting Commissioner of Patents and Trademarks*